US012372257B2

(12) United States Patent
Murray

(10) Patent No.: US 12,372,257 B2
(45) Date of Patent: Jul. 29, 2025

(54) AIR TREATMENT SYSTEM

(71) Applicant: Darren Clifford Murray, Sears, MI (US)

(72) Inventor: Darren Clifford Murray, Sears, MI (US)

(*) Notice: Subject to any disclaimer, the term of this patent is extended or adjusted under 35 U.S.C. 154(b) by 378 days.

(21) Appl. No.: 17/457,655

(22) Filed: Dec. 4, 2021

(65) Prior Publication Data

US 2023/0175719 A1   Jun. 8, 2023

(51) Int. Cl.
*B01D 53/02* (2006.01)
*A61L 9/20* (2006.01)
*F24F 8/22* (2021.01)

(52) U.S. Cl.
CPC ............... *F24F 8/22* (2021.01); *A61L 9/20* (2013.01); *A61L 2209/12* (2013.01)

(58) Field of Classification Search
CPC ........... F24F 8/22; A61L 9/20; A61L 2209/12
See application file for complete search history.

(56) References Cited

U.S. PATENT DOCUMENTS

| 7,652,265 B2 * | 1/2010 | Subbarao ................. A61L 9/20 96/224 |
| 9,295,741 B2 * | 3/2016 | Yerby ....................... A61L 2/24 |
| 11,000,622 B2 | 5/2021 | Krosney |
| 11,040,123 B2 | 6/2021 | Li et al. |
| 11,590,358 B2 * | 2/2023 | Osypka ................ A61N 5/0603 |
| 2011/0005620 A1 * | 1/2011 | Nevin ..................... A61L 9/20 137/565.18 |
| 2015/0203368 A1 * | 7/2015 | Lee ............................ B08B 1/30 250/435 |
| 2016/0296650 A1 * | 10/2016 | Liao .......................... A61L 2/10 |
| 2017/0224865 A1 * | 8/2017 | Ronda ..................... A61L 9/205 |
| 2020/0009286 A1 | 1/2020 | Zarcone et al. |
| 2020/0282086 A1 * | 9/2020 | Silverman ............... A61L 9/015 |
| 2021/0196851 A1 | 7/2021 | Khan |
| 2021/0228762 A1 | 7/2021 | Eide et al. |
| 2022/0040363 A1 * | 2/2022 | Ling .......................... A61L 9/20 |
| 2022/0040365 A1 * | 2/2022 | Schowalter ........ B01D 46/0028 |
| 2022/0120458 A1 * | 4/2022 | Lee ......................... B01J 19/123 |
| 2022/0133942 A1 * | 5/2022 | Benedek ................. A61L 9/205 422/121 |
| 2022/0211897 A1 * | 7/2022 | Wills, Jr. ............. B01D 53/007 |
| 2022/0256961 A1 * | 8/2022 | Kaplan ................... A62B 23/02 |
| 2023/0233726 A1 * | 7/2023 | Rosenørn ................ A61L 9/015 422/186.3 |

* cited by examiner

Primary Examiner — Christopher P Jones
(74) Attorney, Agent, or Firm — DELEVIE LAW, PLC

(57) ABSTRACT

An air treatment system includes a housing defining a disinfection chamber disposed between an air intake and an air discharge, and a blower in the disinfection chamber adapted to move air through the disinfection chamber along a nominal flow axis. A pair of LED emitters in the disinfection chamber each generate a beam of UV-C light along a beam center axis having a spacial distribution of direct UV-C light characterized by major and minor axes, with the beam center axis of one emitter being generally perpendicular to the nominal flow axis and generally perpendicular to the other beam center axis, the generated spacial distributions of direct UV-C light at least partially overlapping one another within the disinfection chamber, and a reference plane containing one LED emitter's beam center and major axes is generally perpendicular to another reference plane containing the other LED emitter's beam center and major axes.

11 Claims, 4 Drawing Sheets

AIR TREATMENT SYSTEM

FIELD OF THE INVENTION

Figures 1, 2:
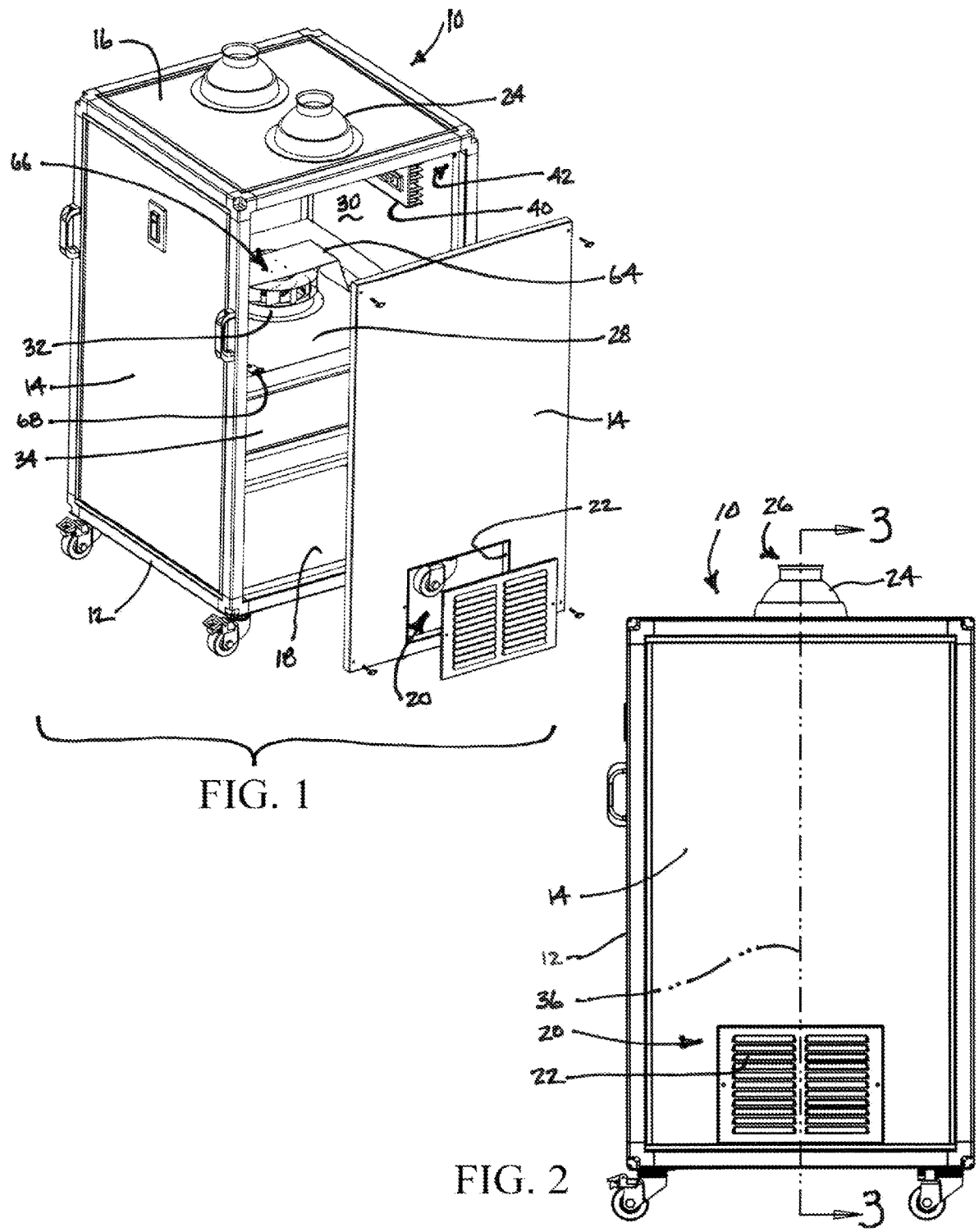

This invention relates generally to air treatment systems used to destroy airborne pathogens including viruses that may be circulating within an enclosed space or indoor environment, such as a classroom, auditorium or building.

BACKGROUND OF THE INVENTION

Airborne pathogens including viruses and other organisms can spread disease. While high efficiency particle absorbing (HEPA) physical filters may be used to remove entrained contaminants larger than about 0.3 microns in size from a forced air stream, certain airborne pathogens including many viruses, such as the SARS-CoV-2 coronavirus and various influenza viruses, are small enough to pass through such filters. Further reducing the relative mesh size of such physical filters is impractical, for at least the reasons of dramatically greater cost, reduced filter life, increased resistance to flow (a significant concern as the desired number of air changes per hour increases), and an increased potential for re-introduction of organic pollutants into the air stream in the event that such pollutants are able to grow on the surface of the filter media. In response, known air purification systems may combine physical filtering with either ozone or photoelectrochemical oxidation, or irradiation with germicidal "deep-ultraviolet" or "far ultraviolet" light, to destroy organic pollutants which remain after filtration, but such systems have only limited effectiveness for destroying airborne pathogens such as the SARS-CoV-2 coronavirus and various influenza viruses in certain indoor environments, given the relatively short time and manner of exposure of non-filtered organic pollutants to oxidation or germicidal irradiation and the number of air changes per hour that are achievable with such systems.

SUMMARY OF THE INVENTION

It is an object of the invention to provide an improved air treatment system for destroying airborne pathogens, including viruses such as the SARS-CoV-2 coronavirus and various influenza viruses, that may be present within an enclosed space or an indoor environment, such as a classroom, auditorium or building.

An air treatment system in accordance with the invention includes a housing that defines an air intake adapted to receive air from the indoor environment into the housing, an air discharge adapted to return air from within the housing back to the indoor environment, and an enclosed disinfection chamber in communication with the air intake and the air discharge. A blower within the housing is adapted to move air through the disinfection chamber along a nominal flow axis from the "upstream" air intake toward the "downstream" air discharge. By way of example, in a preferred embodiment, the blower is mounted within the disinfection chamber itself and includes a centrifugal fan to mix and advantageously induce turbulent flow of air within the disinfection chamber.

A first LED emitter mounted within the disinfection chamber, for example, on a first interior surface of the disinfection chamber as defined by a side panel of the housing, generates an ultraviolet light beam having a wavelength between about 240 nm and about 300 nm, and preferably about 265 nm, to thus create a first spacial distribution of direct UV-C light within the disinfection chamber that is nominally centered about a first beam center axis. A second LED emitter mounted within disinfection chamber, for example, on a second interior surface of the disinfection chamber as defined by a roof panel of the housing, generates an ultraviolet light beam having a wavelength between about 240 nm and about 300 nm, and preferably about 265 nm, to thus create a second spacial distribution of direct UV-C light nominally centered about a second beam center axis, with the second spacial distribution of direct ultraviolet light at least partially overlapping the first spacial distribution of direct ultraviolet light.

In accordance with an aspect of the invention, in a preferred embodiment, the center axis of the UV-C beam generated by the first emitter is generally perpendicular to the nominal flow axis of the disinfection chamber, and the center axis of the beam generated by the second emitter is generally perpendicular to the first beam center axis. Also in a preferred embodiment, the first beam center axis intersects the second beam center axis. The second beam center axis may also be generally collinear with the nominal flow axis.

In accordance with a further aspect of the invention, the first and second emitters preferably each include an array of LED elements to respectively generate a spacial distribution of direct ultraviolet light characterized by a major axis and a minor axis, and the emitters are preferably mounted within the disinfection chamber such that a first reference plane containing both the first emitter's beam center axis and major spacial distribution axis is generally perpendicular to a second reference plane containing both the second emitter's beam center axis and major spacial distribution axis. Still further, in a preferred embodiment, the first reference plane is generally orthogonal to the nominal flow axis, and the system's nominal flow axis generally lies within the second reference plane.

In accordance with another aspect of the invention, the air treatment system preferably includes filter media disposed within the housing between the air intake and the disinfection chamber, with the filter media preferably disposed upstream of the blower to thereby reduce both contaminant accretion on the blower fan and potential entrainment of contaminants within the air flow passing through the disinfection chamber. It will be appreciated that the filter media preferably includes in series a macro-particular filter, a carbon filter, and a HEPA filter, by which to remove contaminants from the air flowing through the housing prior to entry of the air flow into the disinfection chamber.

In accordance with yet another aspect of the invention, the air treatment system may further include at least one of an air heating element and an air cooling element disposed in the housing between the air filter and the blower. By way of example, in a preferred embodiment, the housing defines an enclosed temperature control chamber between the air filter and the blower, and the air-heating and/or air-cooling elements are disposed within the temperature control chamber. In the preferred embodiment, air flows from the temperature control chamber to the disinfection chamber only through the blower.

Figure 5:
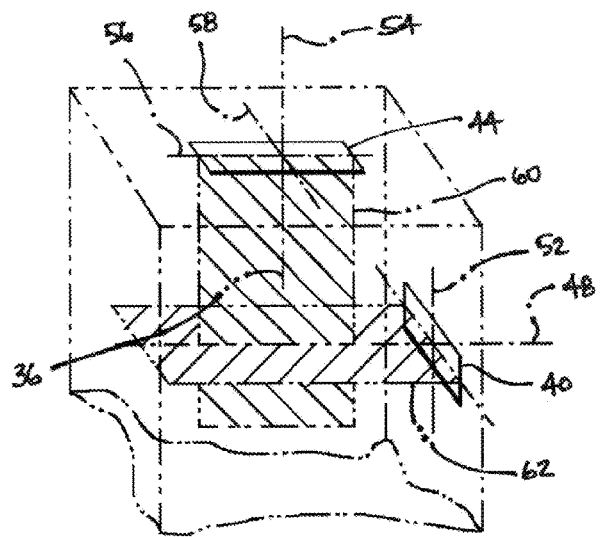

In accordance with yet another aspect of the invention, in a first preferred embodiment, the system's air discharge as defined in a portion of the roof panel includes a pair of spaced discharge nozzles, and the second emitter is mounted on the roof panel's interior surface between the pair of spaced discharge nozzles. In a second preferred embodiment featuring a single air discharge centrally defined in the housing's roof panel, a pair of second emitters are mounted on the roof panel, on either side of the air discharge. In each such case, should the UV-C light beam generated by a roof-mounted emitter impinge directly on any static structures associated with the blower, such as a blower support, such static structures preferably include a reflective surface serving to reflect generated UV-C light about the disinfection chamber to thereby further enhance the destruction of airborne pathogens. It will be appreciated that the disinfection chamber may further include other static structures serving to increase turbulent air flow through the disinfection chamber, thereby ensuring circulation the airborne pathogens through the system's overlapping UV-C light beams; and that such deflectors/turbulators likewise preferably include surfaces capable of reflecting the generated UV-C light throughout the disinfection chamber.

Other objects, features, and advantages of the invention will be readily appreciated upon a review of the subsequent description of the preferred embodiments and the appended claims, taken in conjunction with the accompanying Drawings.

BRIEF DESCRIPTION OF THE DRAWINGS

FIG. 1 is a partially-exploded view in perspective of a first air treatment system in accordance with the invention;

FIG. 2 is a front elevation of the first air treatment system of FIG. 1;

FIG. 3 is a sectional view of the first air treatment system taken along line 3-3 of FIG. 2;

FIG. 4 is a sectional view of the first air treatment system taken along line 4-4 of FIG. 3;

FIG. 5 is a diagrammatic view showing the respective beam center axis, major spacial distribution axis and shared reference plane of each LED emitter of the first air treatment system of FIGS. 1-4;

FIG. 6 is a view in perspective of a second air treatment system in accordance with the invention, shown with its front and side access panels removed for clarity;

FIG. 7 is a front elevational view of the second air treatment system of FIG. 6, again with its front access panel removed; and FIG. 8 is a sectional view of the second air treatment system taken along line 8-8 of FIG. 7.

DETAILED DESCRIPTION OF THE INVENTION

Referring to FIG. 1, a first air treatment system 10 in accordance with the invention for destroying airborne pathogens, including viruses, that may be present within an indoor environment, such as a classroom, auditorium or building, includes a housing 12 formed of a plurality of side panels 14, a roof panel 16 and a floor panel 18. As best seen in FIGS. 1 and 2, a lower portion 20 of each of two opposed side panels 14 defines respective air intakes 22 adapted to receive air from the indoor environment. As best seen in FIG. 3, a pair of spaced nozzles 24 mounted in the roof panel 16 cooperate to define an air discharge 26 adapted to return air from within the housing 12 back to the indoor environment.

Referring again to FIGS. 1 and 3, the housing's side panels 14, roof panel 16 and a further intermediate bulkhead 28 together define an enclosed disinfection chamber 30 that is in communication with both the air intakes 22 through a bulkhead-mounted blower 32 and selected filter media 34, and the roof-mounted discharge nozzles 24. The blower 32 is adapted to move air through the disinfection chamber along a nominal flow axis 36 from the "upstream" air intakes 22 toward the "downstream" air discharge 26. While the invention contemplates any suitable placement of the blower 32 relative to the disinfection chamber 30, by which the blower 32 is operative to generate air flow within the disinfection chamber 30 along the nominal flow axis 36, in the first air treatment system 10, the blower 32 is mounted within the disinfection chamber 30 itself and includes a centrifugal fan 38 which serves to mix and advantageously induce turbulent flow as air passes through the disinfection chamber 30.

It will be appreciated that air directed into the disinfection chamber by the blower 32 will advantageously result in the pressurization of air within the disinfection chamber 30 relative to the indoor environment from which the air is drawn, with the pressurized air within the disinfection chamber 30 thereafter flowing generally along the nominal flow axis 36 and ultimately being exhausted through the discharge nozzles 24. The use of a bulkhead-mounted blower 32 further advantageously ensures that a suitable pressure gradient is generated across the filter media 34, thereby enhancing elimination by the filter media 24 of airborne contaminants prior to entry of the air into the disinfection chamber 30.

Referring to FIGS. 1, 3 and 4, a first LED emitter 40 is mounted within the disinfection chamber 30 on the interior surface 42 of one of the housing's side panels 14. The first LED emitter 40 employs a one-dimensional array of LED's to generate a first ultraviolet light beam having a wavelength between about 240 nm and about 300 nm, and preferably about 265 nm (hereinafter "UV-C light beam"). As best seen in FIGS. 3 and 4, a second LED emitter 44 is mounted within disinfection chamber 30 on the interior surface 46 of the housing's roof panel 16, between the spaced discharge nozzles 24. The second LED emitter 44 similarly employs a one-dimensional array of LED's to generate a second UV-C light beam having a wavelength between about 240 nm and about 300 nm, and preferably about 265 nm.

Referring to the partial diagrammatic view shown in FIG. 5 (the orientation of which is similar to that of FIG. 1), the first UV-C light beam generated by the first LED emitter 40, with its one-dimensional array of LED's, features a beam center axis 48 and a spacial distribution of direct UV-C light that is both nominally centered about the first LED emitter's beam center axis 48 and characterized by a major and minor axis 50,52. The second UV-C light beam generated by the second LED emitter 44, with its respective one-dimensional array of LED's, features a beam center axis 54 and a spacial distribution of direct UV-C light that is both nominally centered about the second LED emitter's beam center axis 54 and characterized by a major and minor axis 56,58.

As seen in both FIGS. 1, 3 and 5, both the first LED emitter's beam center axis 48 and the first LED emitter's major spacial distribution axis 50 are generally perpendicular to the nominal flow axis 36 of the disinfection chamber 30, while both the second LED emitter's beam center axis 54 and the second LED emitter's major spacial distribution axis 56 lie in a vertical reference plane 60 that is generally orthogonal to the beam center axis 48 of the first LED emitter's generated UV-C light beam. FIG. 5 similarly shows that, in the first air treatment system 10, both the first LED emitter's beam center axis 48 and major spacial distribution axis 50 lie in a horizontal reference plane 62 that is both generally orthogonal to the nominal flow axis 36 and generally perpendicular to the vertical reference plane 60 defined by the second LED emitter's beam center axis 54 and major spacial distribution axis 50.

Referring again to FIG. 3, in the first air treatment system 10, the second LED emitter's beam center axis 54 is generally collinear with the nominal flow axis 36 of air through the disinfection chamber 30. And, from the intersection of the vertical and horizontal reference planes 60,62 as shown diagrammatically in FIG. 5, it will be appreciated that, in the first air treatment system 10, the first LED emitter's beam center axis 48 intersects the second LED emitter's beam center axis 54, and that the spacial distribution of direct UV-C light generated by the roof-mounted second LED emitter 40 partially overlaps the spacial distribution of direct UV-C light generated by the side-mounted first LED emitter 44.

Figure 3:
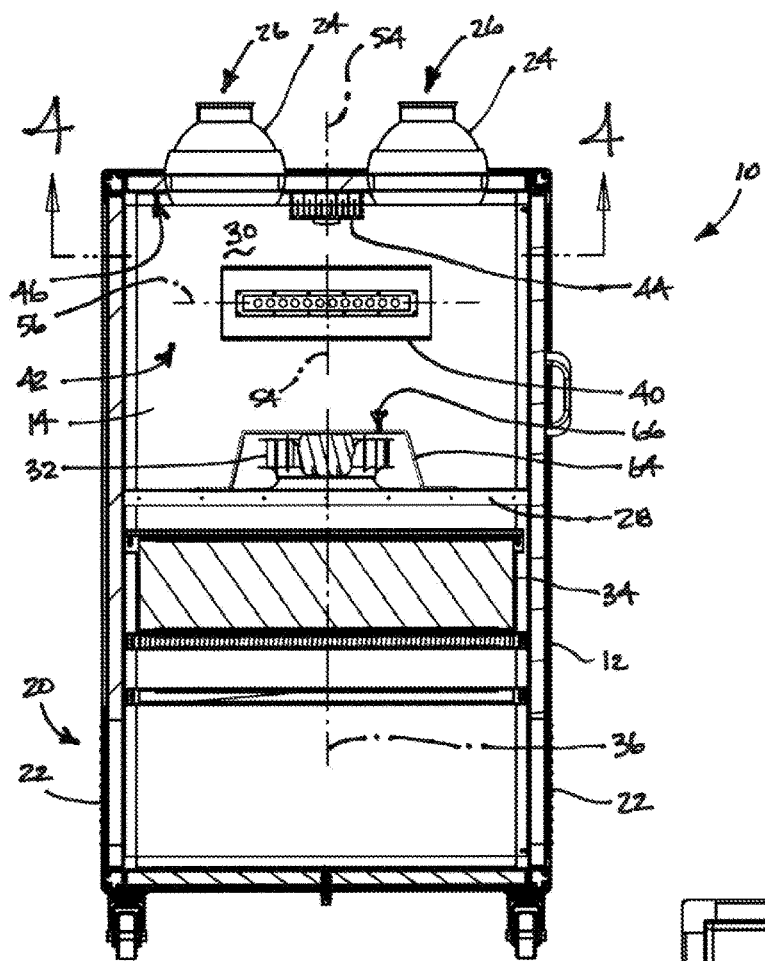
Figure 4:
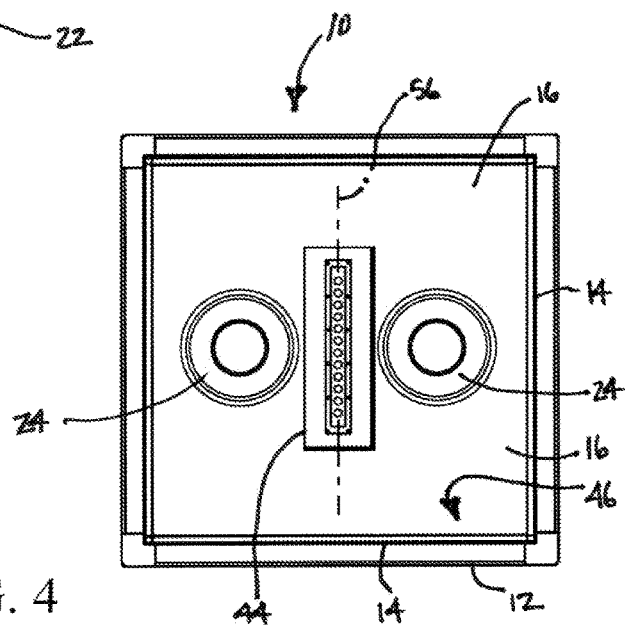

Referring again to FIGS. 1 and 3, the side panels 14, roof panel 16 and bulkhead 28 defining the disinfection chamber 30 are preferably made of a reflective material, such as polished or milled aluminum, or otherwise provided with a coating (not shown) adapted to reflect generated UV-C light about the disinfection chamber 30, to thereby enhance the destruction of airborne pathogens through indirect UV-C irradiation. Additionally, in the event that such generated UV-C light directly impinges on any static structures within the disinfection chamber 30, such as a blower support 64, such static structures preferably include a reflective surface 66 serving to reflect generated UV-C light about the disinfection chamber to similarly enhance the destruction of airborne pathogens. It will be appreciated that the disinfection chamber 30 may further include other static structures serving to increase turbulent air flow through the disinfection chamber, thereby improving circulation of airborne pathogens through the system's overlapping direct UV-C light beams; and that such deflectors/turbulators likewise preferably include surfaces capable of reflecting the generated UV-C light throughout the disinfection chamber.

In order to prevent harm resulting from the unintended escape of the generated UV-C light from within the disinfection chamber 30 upon removal of a side (access) panel 14, the first air treatment system 10 includes a limit switch 68 mounted on the housing 12 adapted to de-power the LED emitters 40,44 in the event of the opening/removal of the side panel 14.

Figure 6:
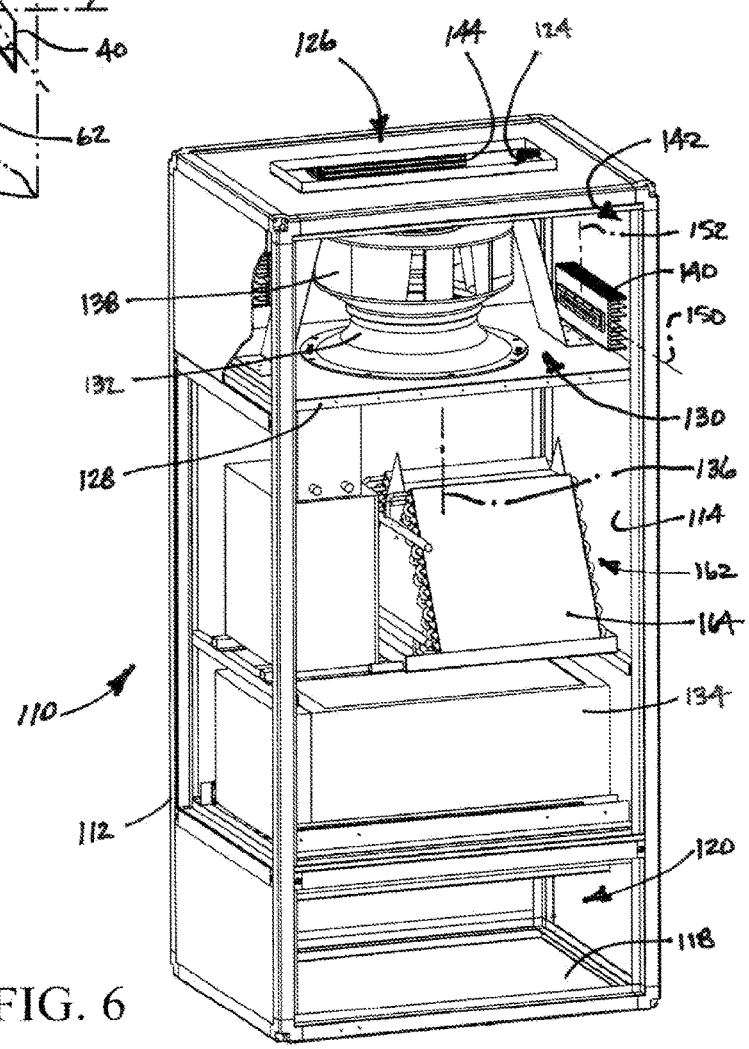
Figure 7:
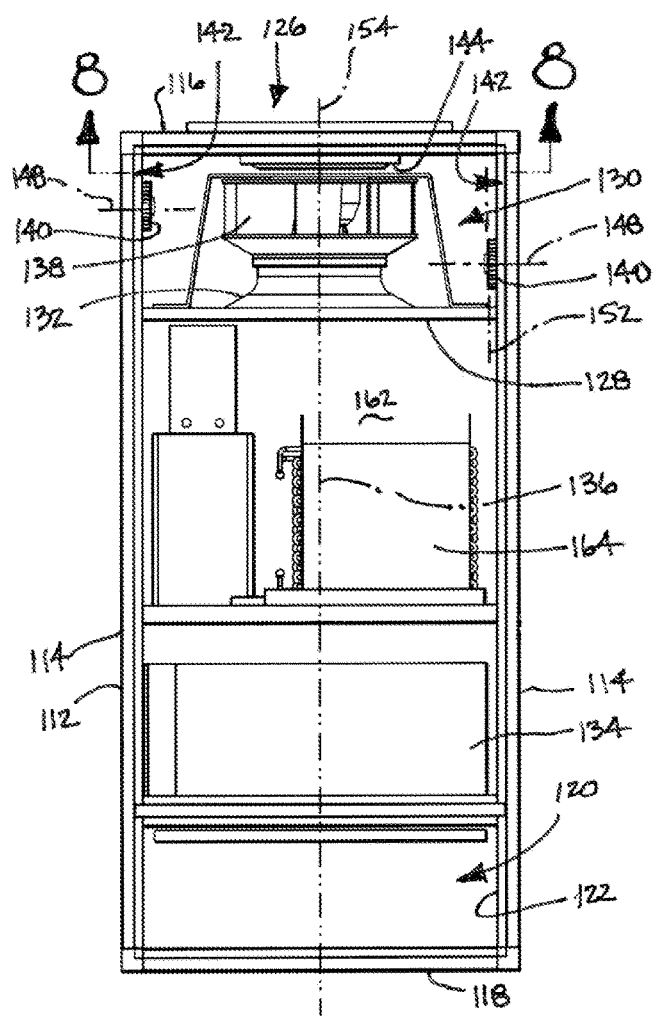
Figure 8:
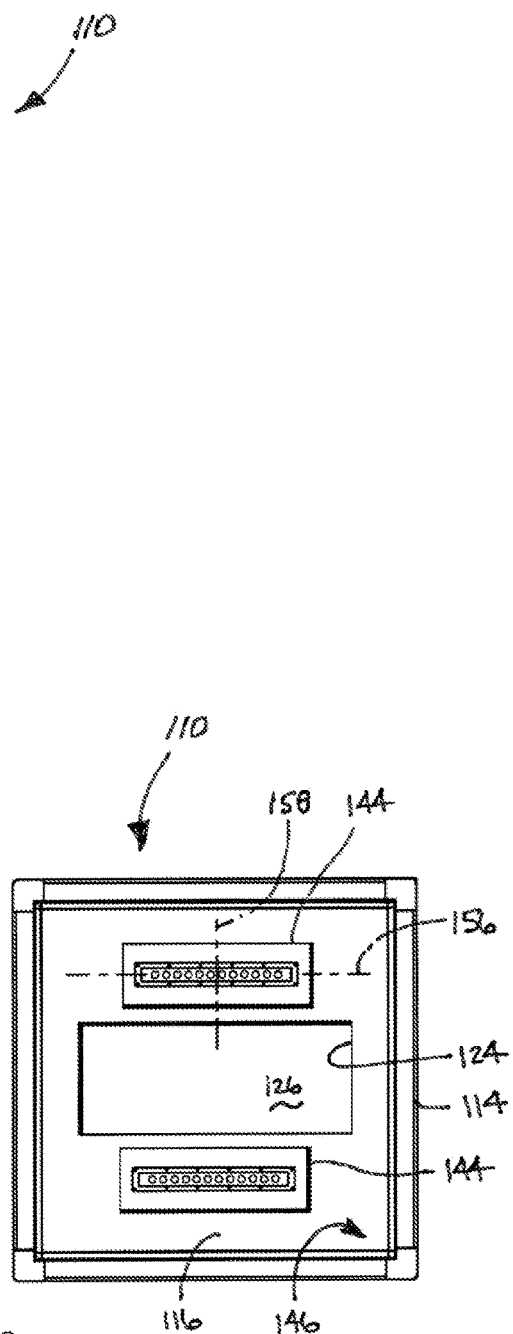

FIGS. 6-8 show a second air treatment system 110 in accordance with the invention, intended for integration within a forced-air heating-and-cooling system (not shown). The second air treatment system 110 includes a housing 112 formed of a plurality of side panels 114, a roof panel 116 and a floor panel 118. As best seen in FIGS. 6 and 7, a lower portion 120 of one side panel 14 defines an air intake 122 adapted to receive air from the indoor environment via a cold-air return (not shown). As best seen in FIGS. 6 and 8, a centralized elongated opening 124 in the roof panel 116 defines an air discharge 126 adapted to return air from within the housing 112 via a supply plenum (not shown) back to the indoor environment.

Referring again to FIGS. 6 and 7, the housing's side panels 114, roof panel 116 and a first intermediate bulkhead 128 together define an enclosed disinfection chamber 130 that is in communication with both the air intake 122 through a bulkhead-mounted blower 132 and selected filter media 134, and the roof-mounted air discharge 126. The blower 132 is adapted to move air through the disinfection chamber along a nominal flow axis 136 from the "upstream" air intake 122 toward the "downstream" air discharge 126. As in the first air treatment system 10 described above, in the second air treatment system 110, the blower 132 is mounted within the disinfection chamber 130 itself and includes a centrifugal fan 138 which serves to mix and advantageously induce turbulent flow of air as it flows through the disinfection chamber 130.

Referring to FIGS. 7 and 8, a pair of first LED emitters 140 are respectively mounted within the disinfection chamber 130 on opposite interior surfaces 142 defined by the housing's side panels 114. Each first LED emitter 140 employs a horizontally-extending one-dimensional array of LED's to generate a respective UV-C light beam having a wavelength between about 240 nm and about 300 nm, and preferably about 265 nm, a generally horizontally-extending beam center axis 148 and a spacial distribution of direct UV-C light that is both nominally centered about the first LED emitter's beam center axis 148 and characterized by a major and minor axis 150,152. As best seen in FIG. 7, one of the first LED emitters 140 is mounted higher on its respective side panel surface 142 than the other, such that the first LED emitters 140 are not mounted in direct horizontal opposition to one another (to thus avoid potentially deleterious interference between their respective generated UV-C light beams).

Referring to FIGS. 7 and 8, a pair of second LED emitters 144 is mounted within disinfection chamber 130 on the interior surface 146 of the housing's roof panel 116, each being positioned on a respective side of the air discharge opening 124. Each second LED emitter 144 similarly employs a one-dimensional array of LED's to generate a second UV-C light beam having a wavelength between about 240 nm and about 300 nm, and preferably about 265 nm. The UV-C light beam generated by each of the second LED emitters 144 features a beam center axis 154 and a spacial distribution of direct UV-C light that is both nominally centered about the second LED emitter's beam center axis 154 and characterized by a major and minor axis 156,158, with the major spacial distribution axis 156 of each second LED emitter 144 extending in a direction generally parallel to the elongated opening 124 that defines the air discharge 126.

As best seen in FIG. 7, the beam center axis 148 of each side-mounted first LED emitter 140 is generally perpendicular to the nominal flow axis 136 within the disinfection chamber 130, while the beam center axis 154 and major spacial distribution axis 156 of each roof-mounted second LED emitter 144 define a vertical reference plane 160 that is generally orthogonal to the beam center axis 148 of each first LED emitter's generated UV-C light beam. It will also be appreciated that, in the second air treatment system 110, the spacial distribution of direct UV-C light generated by each roof-mounted second LED emitter 140 partially overlaps the spacial distribution of direct UV-C light generated by each of the side-mounted first LED emitter 144.

Returning again to FIGS. 6 and 7, in the second air treatment system 110, the housing 112 further defines a second enclosed chamber 162 between of the filter media 134 and the bulkhead-mounted blower 132. An electric compressor/condenser set 164 supported within the second chamber 162 is adapted to selectively heat or cool the air flowing into the disinfection chamber 130.

While the above description constitutes the preferred embodiments, it will be appreciated that the invention is susceptible to modification, variation and change without departing from the proper scope and fair meaning of the subjoined claims.

I claim:

1. An air treatment system for treating air contained within an indoor environment, the system comprising:
   a housing defining an air intake adapted to receive air from the indoor environment into the housing, an air discharge adapted to return air from within the housing back to the indoor environment, and an enclosed disinfection chamber in communication with the air intake and the air discharge;

a blower adapted to move air through the disinfection chamber along a nominal flow axis from the air intake to the air discharge;

a first LED emitter mounted within the disinfection chamber generating an ultraviolet light beam having a wavelength between about 240 nm and about 300 nm and a first spacial distribution of direct ultraviolet light about a first beam center axis; and a second LED emitter mounted within the disinfection chamber generating an ultraviolet light beam having a wavelength between about 240 nm and about 300 nm and a second spacial distribution of direct ultraviolet light about a second beam center axis, wherein the first beam center axis is generally perpendicular to the nominal flow axis and the second beam center axis is generally perpendicular to the first beam center axis, wherein the second spacial distribution of direct ultraviolet light at least partially overlaps the first spacial distribution of direct ultraviolet light within the disinfection chamber, wherein the first and second emitters each include an array of LED elements, whereby the spacial distribution of direct ultraviolet light respectively generated by the first and second emitters is characterized by a major axis and a minor axis, and wherein a first reference plane containing the first beam center axis and the major axis of the first spacial distribution of ultraviolet light is generally perpendicular to a second reference plane containing the second beam center axis and the major axis of the second spacial distribution of direct ultraviolet light.

2. The air treatment system of claim 1, wherein the first reference plane is generally orthogonal to the nominal flow axis.

3. The air treatment system of claim 2, wherein the nominal flow axis generally lies within the second reference plane.

4. The air treatment system of claim 1, wherein the array of LED elements of at least one of the first and second emitters is a one-dimensional array of LED elements.

5. The air treatment system of claim 4, wherein the first beam center axis intersects the second beam center axis.

6. The air treatment system of claim 1, wherein the housing includes a plurality of panels secured together to form the disinfection chamber, a first one of the panels defining a first interior surface of the disinfection chamber and a second one of the panels defining a second interior surface of the disinfection chamber; and wherein the air discharge is defined in a portion of the second one of the panels, the air discharge includes a first discharge nozzle, and the second emitter is mounted on the second interior surface of the disinfection chamber adjacent to the first discharge nozzle.

7. The air treatment system of claim 6, wherein the air discharge further includes a second discharge nozzle defined in the portion of the second one of the panels, the second discharge nozzle being spaced from the first discharge nozzle; and wherein the second emitter is mounted on the second interior surface of the disinfection chamber between the first and second discharge nozzles.

8. The air treatment system of claim 6, wherein the blower is mounted within the disinfection chamber upstream of the second emitter, and further including a reflective element disposed between the blower and the second emitter, the reflective element reflecting at least a portion of the ultraviolet light generated by the second emitter away from the blower.

9. The air treatment system of claim 1, further including an air filter disposed in the housing between the air intake and the disinfection chamber.

10. The air treatment system of claim 9, further including at least one of an air heating element and an air cooling element disposed in the housing between the air filter and the blower.

11. The air treatment system of claim 10, wherein the housing defines an enclosed temperature control chamber between the air filter and the blower, the temperature control chamber containing the at least one of the air heating element and the air cooling element; and wherein air flows from the temperature control chamber to the disinfection chamber only through the blower.

* * * * *